(12) United States Patent
Zhang et al.

(10) Patent No.: US 12,329,744 B2
(45) Date of Patent: Jun. 17, 2025

(54) METHODS OF PREPARING EXTRUDATES

(71) Applicant: BOARD OF REGENTS, THE UNIVERSITY OF TEXAS SYSTEM, Austin, TX (US)

(72) Inventors: Feng Zhang, Pflugerville, TX (US); Abbe Miller, Austin, TX (US); Siyuan Huang, Austin, TX (US); Robert O. Williams, III, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 600 days.

(21) Appl. No.: 17/162,230

(22) Filed: Jan. 29, 2021

(65) Prior Publication Data
US 2021/0154172 A1 May 27, 2021

Related U.S. Application Data

(62) Division of application No. 14/858,410, filed on Sep. 18, 2015, now abandoned.
(Continued)

(51) Int. Cl.
*A61K 31/4184* (2006.01)
*A61J 3/10* (2006.01)
(Continued)

(52) U.S. Cl.
CPC .............. *A61K 31/4184* (2013.01); *A61J 3/10* (2013.01); *A61K 9/1635* (2013.01);
(Continued)

(58) Field of Classification Search
CPC .............. A61K 31/4184; A61K 9/1635; A61K 9/2027; A61K 9/2054; A61K 9/2095;
(Continued)

(56) References Cited

U.S. PATENT DOCUMENTS 5,456,923 A * 10/1995 Nakamichi .......... A61K 9/1694
514/774
6,221,368 B1 4/2001 Breitenbach et al.
(Continued)

FOREIGN PATENT DOCUMENTS

| CA | 2363071 | 6/2001 |
| WO | WO 1995/013794 | 5/1995 |

(Continued)

OTHER PUBLICATIONS

Allen, "The biopharmaceutics classification system and compounding pharmacy: Part II", International Journal of Pharmaceutical Compounding, 3(9): 4 pgs., 2013.
(Continued)

*Primary Examiner* — Trevor Love
(74) *Attorney, Agent, or Firm* — Parker Highlander PLLC

(57) ABSTRACT

Compositions and methods of preparing amorphous drug formulations through hot melt extrusion which result in decreased decomposition of the desired drug are provided herein. Also provided are methods and compositions which further comprise a pharmaceutically acceptable thermoplastic polymer. In some embodiments, these compositions comprise a therapeutically active agent which is only sparingly soluble in water.

18 Claims, 4 Drawing Sheets

| Screw element | Type of screw | Function |
|---|---|---|
| 1 | GFA 3-15-30 | Conveying |
| 2 | GFA 3-20-30 | Conveying |
| 3 | GFA 3-20-30 | Conveying |
| 4 | GFA 3-15-30 | Conveying |
| 5 | GFA 3-15-30 | Conveying |
| 6 | GFA 3-15-30 | Conveying |
| 7 | KB 7-3-15-60F | Mixing |
| 8 | KB 7-3-15-60F | Mixing |
| 9 | GFA 3-15-30 | Conveying |
| 10 | GFA 3-20-30 | Conveying |
| 11 | Mixing element | Pure mixing |
| 12 | KB 7-3-15-30F | Mixing |
| 13 | KB 7-3-15-30F | Mixing |
| 14 | GFA 3-10-30 | Conveying |
| 15 | GFA 3-10-30 | Conveying |
| 16 | GFA 3-10-30 | Conveying |

Related U.S. Application Data

(60) Provisional application No. 62/213,041, filed on Sep. 1, 2015, provisional application No. 62/052,563, filed on Sep. 19, 2014.

(51) Int. Cl.
| | |
|---|---|
| *A61K 9/16* | (2006.01) |
| *A61K 9/20* | (2006.01) |
| *A61K 31/192* | (2006.01) |
| *B29C 48/00* | (2019.01) |
| *C08L 1/02* | (2006.01) |
| *C08L 1/28* | (2006.01) |
| *B29K 105/00* | (2006.01) |

(52) U.S. Cl.
CPC .......... *A61K 9/2027* (2013.01); *A61K 9/2054* (2013.01); *A61K 9/2095* (2013.01); *A61K 31/192* (2013.01); *C08L 1/02* (2013.01); *C08L 1/284* (2013.01); *B29C 48/023* (2019.02); *B29K 2105/0035* (2013.01); *B29K 2995/0059* (2013.01)

(58) Field of Classification Search
CPC . A61K 31/192; A61J 3/10; C08L 1/02; C08L 1/284; B29C 48/023; B29K 2105/0035; B29K 2995/0059
See application file for complete search history.

(56) References Cited

U.S. PATENT DOCUMENTS

| | | |
|---|---|---|
| 6,499,984 B1 | 12/2002 | Ghebre-Sellassie et al. |
| 7,122,143 B2 | 10/2006 | Sowden et al. |
| 7,607,596 B1 | 10/2009 | Ghebre-Sellassie et al. |
| 7,625,507 B2 | 12/2009 | Ray et al. |
| 8,052,899 B2 | 9/2011 | Berndl et al. |
| 8,372,836 B2 | 2/2013 | Ketner et al. |
| 2007/0246867 A1 | 10/2007 | Nelson et al. |
| 2008/0280999 A1 | 11/2008 | Lakshman |
| 2009/0098200 A1 | 4/2009 | Krayz et al. |
| 2010/0047340 A1 | 2/2010 | McGinity et al. |
| 2013/0248614 A1 | 9/2013 | Maskrot et al. |

FOREIGN PATENT DOCUMENTS

| | | |
|---|---|---|
| WO | WO 97/49384 | 12/1997 |
| WO | WO 98/18610 | 5/1998 |
| WO | WO 02/35991 | 5/2002 |
| WO | WO 2010/060667 | 6/2010 |
| WO | WO 2011/159626 | 12/2011 |
| WO | WO 2013/040187 | 3/2013 |

OTHER PUBLICATIONS

International Search Report and Written Opinion issued in International Application No. PCT/US15/50955, mailed Dec. 18, 2015.
Extended European Search Report and Written Opinion issued in European Application No. 15 84 2831.8, dated Apr. 18, 2018.
Williams Declaration under 37 CFR 1.132 filed Apr. 17, 2018, in U.S. Appl. No. 14/858,410.

\* cited by examiner

| Screw element | Type of screw | Function |
|---|---|---|
| 1 | GFA 3-15-30 | Conveying |
| 2 | GFA 3-20-30 | Conveying |
| 3 | GFA 3-20-30 | Conveying |
| 4 | GFA 3-15-30 | Conveying |
| 5 | GFA 3-15-30 | Conveying |
| 6 | GFA 3-15-30 | Conveying |
| 7 | KB 7-3-15-60F | Mixing |
| 8 | KB 7-3-15-60F | Mixing |
| 9 | GFA 3-15-30 | Conveying |
| 10 | GFA 3-20-30 | Conveying |
| 11 | Mixing element | Pure mixing |
| 12 | KB 7-3-15-30F | Mixing |
| 13 | KB 7-3-15-30F | Mixing |
| 14 | GFA 3-10-30 | Conveying |
| 15 | GFA 3-10-30 | Conveying |
| 16 | GFA 3-10-30 | Conveying |

Screw Design: 2x GFA3-30-20, 1x GFA3-30-15, 2x GFA3-30-10, 1x KB7-3-15-30°, 1x KB7-3-15-90°, 1x GFA3-15-15-L, 2x GFA3-30-20, 1x KB7-3-15-30°, 1x Mixing Block-30, 1x KB7-3-15-30°, 1x KB7-3-15-90°, 1x GFA3-30-15, 2x GFA3-30-10

Screw Design: 2x GFA3-30-20, 1x GFA3-30-15, 2x GFA3-30-10, 1x KB7-3-15-30°, 1x KB7-3-15-90°, 1x GFA3-15-15-L, 2x GFA3-30-20, 1x KB7-3-15-30°, 1x Mixing Block-30, 1x KB7-3-15-30°, 1x KB7-3-15-90°, 1x GFA3-30-15, 2x GFA3-30-10

METHODS OF PREPARING EXTRUDATES

This application is a divisional of U.S. patent application Ser. No. 14/858,410, filed Sep. 18, 2015, which claims the benefit of United States Provisional Patent Application Nos. 62/052,563, filed Sep. 19, 2014, and 62/213,041, filed Sep. 1, 2015. The entirety of each of the applications listed above is incorporated herein by reference.

BACKGROUND OF THE INVENTION

1. Field of the Invention

The present invention relates generally to the field of pharmaceuticals and pharmaceutical manufacture. More particularly, it concerns compositions and methods of preparing a drug composition.

2. Description of Related Art

Two common methods of preparing drug compositions are spray drying and hot melt extrusion. Hot melt extrusion is preferred as this method can process large amounts of the therapeutically active agent, helps preserve the amorphous nature of the material, and is solvent free. In order to extrude the product, the extruder applies large amounts of energy to the drug composition in the form of heat and mechanical energy. This energy is known to degrade many different types of therapeutically active agents. For these agents, spray drying must be used to prepare formulations. Spray drying though has many disadvantages such as the use of large amounts of solvent, the inability to process more than 20% w/w solid material in the drug composition, and the use of large and expensive equipment. These hurdles represent a bottleneck in the manufacture of certain drugs. Thus, there is still a need to obtain a method of preparing drugs through hot melt extrusion which reduces the degradation of the therapeutically active agent in the composition.

SUMMARY OF THE INVENTION

In some aspects, the present disclosure provides compositions for use in a hot melt extrusion process which results in decreased decomposition of the therapeutically active agent. In other aspects, the miscibility between the therapeutically active agent and polymer is enhanced, such as with a high melting point therapeutically active agent. In other aspects, the presence of solvent improves processing conditions; including reduced temperature and reduced torque required in the hot melt extrusion process. Also, provided are methods of preparing extrudates using these compositions.

In some aspects, the present disclosure provides extrusion stock material compositions comprising:
- (a) a mixture of a therapeutically active agent and a pharmaceutically acceptable thermoplastic polymer comprising from about 0.5% to about 55% w/w of a therapeutically active agent; and
- (b) an organic solvent;

wherein the composition has a glass transition temperature ($T_g$) from about 40° C. to about 100° C. In some embodiments, the glass transition temperature is from about 70° C. to about 90° C. In some embodiments, the glass transition temperature is about 80° C.

In some embodiments, the amount of organic solvent is from about 0.5% w/w to about 45% w/w. In some embodiments, the amount of organic solvent is from 1% w/w to about 30% w/w. In some embodiments, the therapeutically active agent is soluble in the organic solvent. In some embodiments, the therapeutically active agent and the pharmaceutically acceptable thermoplastic polymer are soluble in the organic solvent. In some embodiments, the therapeutically active agent and the pharmaceutically acceptable thermoplastic polymer have similar solubility in the organic solvent. In some embodiments, the organic solvent is a volatile organic solvent. In some embodiments, the organic solvent is a polar solvent. In some embodiments, the organic solvent has a boiling point of less than about 100° C. In some embodiments, the organic solvent is a polar hydrocarbon. In some embodiments, the organic solvent is a haloalkane such as dichloromethane. In other embodiments, the organic solvent is a polar aprotic solvent. In some embodiments, the organic solvent is acetone. In other embodiments, the organic solvent is an ether such as tetrahydrofuran. In other embodiments, the organic solvent is a polar protic solvent such as an alcohol. In some embodiments, the organic solvent is methanol, ethanol, or isopropanol. In some embodiments, the organic solvent comprises a mixture of two or more different organic solvents. In some embodiments, the organic solvent is a mixture of solvents comprising at least one solvent selected from the group consisting of methanol, ethanol, isopropanol, acetone, tetrahydrofuran, or dichloromethane. In some embodiments, the mixture of solvents comprises two or more solvents selected from the group consisting of methanol, ethanol, isopropanol, acetone, tetrahydrofuran, or dichloromethane. In some embodiments, the organic solvent is a mixture with water. In some embodiments, the compositions do not contain or is substantially free of a supercritical fluid. In some embodiments, the compositions are essentially free of any supercritical fluids.

In some embodiments, the compositions comprise from about 55% to about 99.5% of a mixture of a therapeutically active agent and a pharmaceutically acceptable thermoplastic polymer. In some embodiments, the compositions comprise a mixture of an amorphous therapeutically active agent and a pharmaceutically acceptable thermoplastic polymer. In other embodiments, the compositions comprise a therapeutically active agent. In other embodiments, the compositions comprise a therapeutically active agent which is rendered into the amorphous form following extrusion. In some embodiments, the pharmaceutically acceptable thermoplastic polymer is a cellulosic polymer. In some embodiments, the pharmaceutical thermoplastic polymer is a neutral cellulosic polymer such as hydroxypropyl cellulose, hydroxypropyl methyl cellulose, hydroxyethyl cellulose, or hydroxymethyl cellulose. In some embodiments, the pharmaceutical thermoplastic polymer is hydroxypropyl methyl cellulose. In other embodiments, the pharmaceutical thermoplastic polymer is an ionizable cellulosic polymer such as cellulose acetate phthalate or hydroxypropyl methyl cellulose acetate succinate. In some embodiments, the pharmaceutical thermoplastic polymer is hydroxypropyl methyl cellulose acetate succinate. In other embodiments, the pharmaceutically acceptable thermoplastic polymer is a non-cellulosic polymer. In some embodiments, the pharmaceutically acceptable thermoplastic polymer is a neutral non-cellulosic polymer such as poly(vinyl alcohol), poly(carboxylate), poly(ethylene glycol), poly(propylene glycol), polyvinyl pyrrolidone, copovidone, poloxamer, polymethylacrylate, or polyacrylate. In some embodiments, the pharmaceutically acceptable thermoplastic polymer is polyvinyl pyrrolidone or copovidone. In other embodiments, the pharmaceutically acceptable thermoplastic polymer is an ionizable non-cellulosic polymer such as an ionizable polymethacrylate or polyacrylate. In some embodiments, the pharmaceutically acceptable thermoplastic polymer is a polymethacrylate or polyacrylate functionalized with a carboxylic acid group. In some embodiments, the pharmaceutically acceptable thermoplastic polymer is an Eudragit® polymer such as Eudragit® L, Eudragit® S, or Eudragit® FS.

In some embodiments, the therapeutically active agent is an active agent which has a solubility in water of less than 5 mg/mL. In some embodiments, the therapeutically active agent is a Biopharmaceutic Classification System Class II or Class IV active agent. In some embodiments, the therapeutically active agent is an agent which is known to undergo thermal degradation. In some embodiments, the therapeutically active agent undergoes degradation at a temperature greater than 80° C. In some embodiments, the compositions further comprise one or more excipients. In some embodiments, the excipient is a lubricant, disintegrant, binder, filler, surfactant, or any combination thereof. In some embodiments, the excipient is a functional excipient selected from the group consisting of lubricant, disintegrant, and surfactant. In other embodiments, the extrusion stock material composition further comprises (a) from about 55% to 99.5% w/w of an amorphous therapeutically active agent or a mixture of an amorphous therapeutically active agent and a pharmaceutically acceptable thermoplastic polymer; and (b) an organic solvent.

In yet another aspect, the present disclosure provides methods of preparing an extrudate comprising:
  (a) obtaining an extrusion stock material composition as described herein; and
  (b) transferring the extrusion stock material composition through an extruder to obtain an extrudate comprising the therapeutically active agent and the organic solvent.

In some embodiments, the extrusion stock material composition is prepared by mixing the therapeutically active agent and the pharmaceutically acceptable thermoplastic polymer and then injecting the solvent online into the mixture of the solids as the extrusion stock material is transferred through the extruder. In some embodiments, the extruder is a single screw extruder, an intermeshing screw extruder, a twin-screw extruder, a thermokinetic mixer, and a kneader. In some embodiments, the methods further comprise heating the extrusion stock material composition as the first composition is transferred through the extruder. In some embodiments, the extrusion stock material composition is heated to a temperature from about 50° C. to about 180° C. In some embodiments, the temperature is from about 80° C. to about 160° C. In some embodiments, the methods further comprise cooling the extrudate to room temperature. In some embodiments, the methods further comprise drying the extrudate to remove the organic solvent. In some embodiments, the extrudate is dried at an elevated temperature. In some embodiments, the extrudate is milled into granules and then dried at an elevated temperature and/or under a vacuum. In some embodiments, the elevated temperature is from about 30° C. to about 100° C. In some embodiments, the extrudate is dried at a reduced pressure. In some embodiments, the reduced pressure is from about 1 kPa to about 100 kPa. In some embodiments, the extrudate is dried at an elevated temperature and at a reduced pressure.

In some embodiments, the method further comprises milling the extrudate to obtain a dry powder or a granule. In some embodiments, the method further comprises formulating the dry powder or granule into a pharmaceutical composition, which may include pellets or beads, capsules, and tablets. In some embodiments, the pharmaceutical composition is formulated for oral administration. In some embodiments, the method comprises applying a torque of less than 85% of the capacity of the motor of the extruder. In some embodiments, the extrusion stock material composition further comprises a pharmaceutically acceptable thermoplastic polymer. In some embodiments, the pharmaceutically acceptable thermoplastic polymer and the therapeutically active agent are added first and then the organic solvent. In some embodiments, the pharmaceutically acceptable thermoplastic polymer and the therapeutically active agent are added after the organic solvent.

In still yet another aspect, the present disclosure provides methods of preparing an extrudate comprising:
  (a) admixing a extrusion stock material composition described herein to a mixing apparatus;
  (b) feeding the extrusion stock material composition through an extruder; and
  (c) extruding the extrusion stock material composition from the press through a die to obtain an extrudate.

In some embodiments, the extruder is a twin-screw extruder. In some embodiments, the extrusion stock material composition is formed by adding the organic solvent as the extrusion stock material composition is transferred through the extruder. In some embodiments, the mixing apparatus is the extruder.

In still another aspect, the present disclosure provides methods of preparing a therapeutically active agent composition containing a therapeutically active agent which decomposes at a temperature greater than 80° C. comprising admixing an extrusion stock material composition containing the therapeutically active agent described herein and extruding the composition to obtain the therapeutically active agent composition.

In still yet another aspect, the present disclosure provides composition prepared according to the methods described herein.

In some aspects, the present disclosure provides composition comprising:
  an amorphous therapeutically active agent dispersed in a polymer; and
  an organic solvent, wherein the organic solvent comprises about 0.5-30% w/w of the composition.

In some embodiments, the therapeutically active agent is poorly soluble in an aqueous environment. In some embodiments, the therapeutically active agent is a Biopharmaceutics Classification System Class II or IV compound. In some embodiments, the amorphous solid dispersion is an extrudate. In some embodiments, the polymer is selected from the group consisting of a neutral non-cellulosic polymer, an ionizable non-cellulosic polymer, an ionizable cellulosic polymer, a neutral cellulosic polymer, and any combination thereof. In some embodiments, the neutral non-cellulosic polymer is selected from the group consisting of polyvinyl pyrrolidone, polyvinyl alcohol, copovidone, and poloxamer. In other embodiments, the ionizable non-cellulosic polymer is selected from the group consisting of carboxylic acid, functionalized polyacrylate, and polymethacrylate. In some embodiments, the polymethacrylate is selected from the group consisting of Eudragit L, Eudragit S, and Eudragit FS. In other embodiments, the ionizable cellulosic polymer is selected from the group consisting of cellulose acetate phthalate and hydroxypropyl methyl cellulose acetate succinate. In other embodiments, the neutral cellulosic polymer is selected from the group consisting of hydroxypropyl cellulose, hydroxypropyl methyl cellulose, hydroxyethyl cellulose, and hydroxymethyl cellulose.

In some embodiments, the organic solvent is miscible with the therapeutically active agent and polymer. In some embodiments, the organic solvent has a boiling point less than about 100° C. In some embodiments, the organic solvent is selected from the group consisting of methanol, ethanol, acetone, isopropyl alcohol, dichloromethane, and any combination thereof. In some embodiments, the compositions further comprise one or more functional excipients. In some embodiments, the functional excipient is a lubricant, a binder, a filler, a disintegrant, a surfactant, or any combination thereof.

In still yet another aspect, the present disclosure provides methods comprising:
combining a therapeutically active agent, a polymer, and an organic solvent in a mixing apparatus thereby forming a mixture, wherein the organic solvent comprises about 5 to about 30% w/w of the mixture;
heating the mixture at a temperature less than about 100° C. to form an extrudate comprising the amorphous solid dispersion.

In some embodiments, the method comprises feeding the therapeutically active agent and the pharmaceutically acceptable thermoplastic polymer into a twin-screw extruder to form a first composition, injecting the organic solvent into the first composition such that the organic solvent comprises about 20% w/w, extruding the first composition under conditions such that a portion of the solvent evaporates as the material is extruded, and further drying the material to remove the remaining organic solvent. In some embodiments, the organic solvent is removed to a level sufficient to allow the composition is to be administered to a patient or approved by health regulatory agencies. In some embodiments, the mixing apparatus is selected from the group consisting of a single screw extruder, an intermeshing screw extruder, a twin-screw extruder, a thermokinetic mixer, and a kneader. In some embodiments, the organic solvent comprises about 0.5 to about 27% w/w of the extrudate prior to a further drying step. In some embodiments, the methods further comprise the step of cooling the extrudate to ambient temperature. In some embodiments, the methods further comprise the step of milling the extrudate into powder and further drying the powder. In some embodiments, the methods further comprise the step of drying the extrudate to reduce the organic solvent content. In some embodiments, the therapeutically active agent is poorly soluble in an aqueous environment. In some embodiments, the therapeutically active agent is a Biopharmaceutics Classification System Class II or IV compound.

In some embodiments, the polymer is selected from the group consisting of a neutral non-cellulosic polymer, an ionizable non-cellulosic polymer, an ionizable cellulosic polymer, a neutral cellulosic polymer, and any combination thereof. In some embodiments, the neutral non-cellulosic polymer is selected from the group consisting of polyvinyl pyrrolidone, polyvinyl alcohol, copovidone, and poloxamer. In some embodiments, the ionizable non-cellulosic polymer is selected from the group consisting of carboxylic acid, functionalized polyacrylate, and polymethacrylate. In some embodiments, the polymethacrylate is selected from the group consisting of Eudragit L, Eudragit S, and Eudragit FS. In some embodiments, the ionizable cellulosic polymer is selected from the group consisting of cellulose acetate phthalate and hydroxypropyl methyl cellulose acetate succinate. In some embodiments, the neutral cellulosic polymer is selected from the group consisting of hydroxypropyl cellulose, hydroxypropyl methyl cellulose, hydroxyethyl cellulose, and hydroxymethyl cellulose.

In some embodiments, the organic solvent is miscible with the therapeutically active agent and polymer. In some embodiments, the organic solvent has a boiling point less than about 100° C. In some embodiments, the organic solvent is selected from the group consisting of methanol, acetonitrile, 2-butanol, 5-butyl alcohol, 1,2-dichloroethane, 1,4-dioxane, isopropanol, methanol, 1-propanol, 2-propanol, ethanol, acetone, isopropyl alcohol, dichloromethane, and any combination thereof. In some embodiments, the mixture further comprises a supercritical fluid. In some embodiments, the mixture further comprises one or more functional excipients. In some embodiments, the functional excipient is a lubricant, a disintegrant, a filler, a binder, a surfactant, or any combination thereof. In some embodiments, the organic solvent is combined with the therapeutically active agent and the polymer after the therapeutically active agent and the polymer are first combined in the mixing apparatus. In other embodiments, the organic solvent is added to the mixing apparatus prior to combining with the therapeutically active agent and the polymer.

In still another aspect, the present disclosure provides systems comprising:
a bulk powder inlet for introducing a therapeutically-active agent and a polymer into a extruder;
a solvent injection line for injecting an organic solvent into the extruder; and
a heating element for heating the extruder to a desired temperature.

In some embodiments, the bulk powder inlet is upstream of the solvent injection line. In other embodiments, the bulk powder inlet is downstream of the solvent injection line. In some embodiments, the extruder is a twin-screw extruder. In some embodiments, the systems further comprise a mixing apparatus in communication with the extruder.

The present disclosure addresses the aforementioned needs by providing a method of manufacturing therapeutic compositions using a combination of thermal compounding and solvent to prepare amorphous solid dispersions.

In one embodiment, an amorphous solid dispersion for use in the manufacture of a therapeutic composition is provided. The amorphous solid dispersion comprises a therapeutically active agent; a polymer; and an organic solvent, wherein the organic solvent used is at 0.5-30% w/w of the drug and polymer blend being processed.

In another embodiment, a method of manufacturing an amorphous solid dispersion is provided. The method comprises the steps of combining a therapeutically active agent, a polymer, and an organic solvent in a mixing apparatus thereby forming a mixture, wherein the organic solvent comprises 5 to 30% w/w of the mixture. The mixture is then processed with an extruder, such as a twin-screw extruder, to form an extrudate comprising the drug, polymer and solvent. In some embodiments, the mixing apparatus is a part of the extruder. The extrudate is then further milled into granules. Granules then undergo drying processes to remove the solvent. Dried granules are then processed along with other excipients into dosage forms suitable for use, such as beads or pellets, tablets, and capsules.

In yet another embodiment, an extruder system adapted for the incorporation of solvents is provided. The extruder system comprises the following: a bulk powder inlet for introducing at least a therapeutically-active agent and a polymer into a mixer; a solvent injection line for injecting an organic solvent (e.g., single or co-solvent system) into the mixer, and a heating element for heating the extruder barrel to a desired temperature. In some embodiments, the mixer is also an extruder.

It is contemplated that any embodiment discussed in this specification can be implemented with respect to any method or composition of the invention, and vice versa. Furthermore, compositions of the invention can be used to achieve the methods of the invention.

The use of the word "a" or "an" when used in conjunction with the term "comprising" in the claims and/or the specification may mean "one," but it is also consistent with the meaning of "one or more," "at least one," and "one or more than one." As used herein "another" may mean at least a second or more.

As used herein, the terms "drug", "pharmaceutical", and "therapeutically active agent" are used interchangeably to represent a compound which invokes a therapeutic or pharmacological effect in a human or animal and is used to treat a disease, disorder, or other condition. In some embodiments, these compounds have undergone and received regulatory approval for administration to a living creature.

The use of the term "or" in the claims is used to mean "and/or" unless explicitly indicated to refer to alternatives only or the alternatives are mutually exclusive. As used herein "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

As used in this specification, the term "significant" (and any form of significant such as "significantly") is not meant to imply statistical differences between two values but only to imply importance or the scope of difference of the parameter.

As used herein references to a "high melting point therapeutically active agent" means a therapeutically active agent with a melting point above 150° C.

Throughout this application, the term "about" is used to indicate that a value includes the inherent variation of error for the device, the method being employed to determine the value, or the variation that exists among the study subjects or experimental studies.

In the context of this application, the term "extrusion stock material" or "extrusion feedstock" are used synonymously and are used to describe a composition which results from mixing a composition comprising a therapeutically active agent, a thermoplastic polymer and an organic solvent that is being processed within an extruder or other thermal processing device to obtain an extrudate. The extrusion stock material may be either mixed before introduction into the extruder or other thermal processing device or mixed within the extruder or other thermal processing device.

As used herein, the term "$T_g$" is the glass transition temperature of the extrusion stock material as readily determined by a skilled artisan, as for example by the wet $T_g$ method using differential scanning calorimetry and hermetically sealed pans to prevent volatilization of the organic solvent.

As used herein, the term "substantially free of" or "substantially free" in terms of a specified component, is used herein to mean that none of the specified component has been purposefully formulated into a composition and/or is present only as a contaminant or in trace amounts. The total amount of all containments, by-products, and other material is present in that composition in an amount less than 2%. The term "more substantially free of" or "more substantially free" is used to represent that the composition contains less than 1% of the specific component. The term "essentially free of" or "essentially free" contains less than 0.1% of the specific component.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements and parameters.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A shows the screw configuration for this example used in the extruder system similar to that shown in FIG. 1. FIG. 4B shows the reduction in torque for specific solvent systems with hypromellose acetate succinate (HPMC-AS).

FIG. 5A shows the screw configuration for this example used in the extruder system similar to that shown in FIG. 1. FIG. 5B shows the powder X-Ray diffraction of extruded naproxen/povidone materials with solvent injection

DESCRIPTION OF ILLUSTRATIVE EMBODIMENTS

Figure 1:
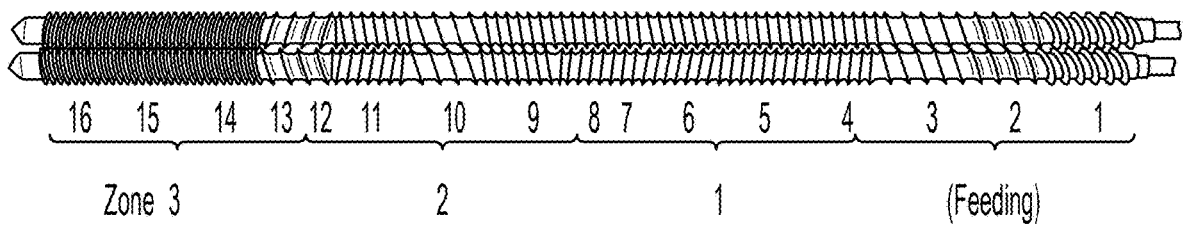
FIG. 1 shows a diagram of an example extruder configuration.

In some aspects of the present disclosure, the methods of using a solvent in a thermal compounding process such as extrusion to prepare pharmaceutical compositions are provided. Without wishing to be bound by any theory, it is believed that the addition of the solvent allows the extrusion stock material composition to be subjected to less thermal and mechanical stress thereby avoiding problems related to degradation of either or both drug and polymer. The mixture of the therapeutically active agent in the solvent along with the pharmaceutically acceptable thermoplastic polymer allows for the formation of a extrusion stock material composition which has a glass transition temperature of less than 120° C. In some embodiments, the use of solvent in the melt extrusion process decreases the viscosity of the mixture such that much of the friction-induced heat generated during the extrusion process is alleviated. In some embodiments, these methods allow for the processing temperatures to be reduced by the presence of a solvent throughout the extrusion process as the solvent reduces the viscosity of the extrusion stock material composition. In some embodiments, the use of solvent in the present methods does not significantly decrease the efficiency of the extrusion process. As described herein, the solvent used may not be substantially evaporated or devolatilized during the extrusion process. In other embodiments, some of the solvent is removed from the extrudate when it exits the die. In some embodiments, the remaining portion of solvent will be removed using secondary drying to a level satisfactory for regulatory purposes.

In the methods described herein, solvent is used and substantially maintained throughout the extrusion process which permits the use of lower processing stress on the materials being processed thereby alleviating degradation of the active agent and polymer. Without wishing to be bound by any theory, it is believed that the addition of solvent to the extrusion stock material composition reduces the amount of torque that must be applied to the mixture to successfully extrude the composition through the die which reduces the energy in the system and thus the amount of degradation.

I. EXTRUSION STOCK MATERIALS AND DRUG COMPOSITION THEREOF

In some aspects, the present disclosure provides methods of preparing an extrusion stock material or extrusion feedstock comprising a therapeutically active agent and an organic solvent. In some embodiments, the extrusion stock material may further comprise a pharmaceutically acceptable thermoplastic polymer. These compositions are then feed into an extruder or extrusion device to obtain an extrudate which may be further processed to obtain a pharmaceutical composition.

In another embodiment, the present disclosure provides methods of manufacturing an amorphous solid dispersion. Solid dispersions are characterized as a molecular dispersion of the therapeutic compound in an inert carrier in a solid state. The method generally comprises the steps of combining a therapeutically active agent, a polymer, and an organic solvent (e.g., single or co-solvent system) in a mixing apparatus thereby forming a mixture. The mixture is then extruded to form an extrudate comprising the amorphous solid dispersion. Additionally, an amorphous solid dispersion for use in the manufacture of a therapeutic composition is provided. The amorphous solid dispersion comprises a therapeutically active agent; a polymer; and an organic solvent, wherein the organic solvent is present upon formation of the amorphous solid dispersion and can be reduced to regulatory acceptable levels by further processing steps.

In some embodiments, the present methods are directed to manufacturing an amorphous solid dispersion that is then further processed to provide the desired end product, such as a pharmaceutical tablet and capsules. An "amorphous solid dispersion" or "solid dispersion" refers to a composition in a solid state that includes one component (active agent) evenly (homogenously) dispersed throughout the other component or components (polymer). The term "solid dispersion" generally encompasses compositions having drugs dispersed in polymer matrix.

In some aspects of the present disclosure, the methods relate to compounds or compositions which do not contain any significant amounts of the active ingredients in their crystalline or microcrystalline state, as evidenced by thermal analysis (DSC) or X-ray diffraction analysis (WAXS). In some embodiments, the active ingredients such as the therapeutically active agent or the pharmaceutically acceptable thermoplastic polymer are in the amorphous form. In some embodiments, the therapeutically active agent is found in the extrudate in the amorphous form.

A. Therapeutically Active Agent

The "therapeutically active agent" used in the present methods and compositions refers to any substance, compound, drug, medicament, or other primary active ingredient that provides a therapeutic or pharmacological effect when administered to a human or animal. Some non-limiting examples of therapeutically active agents are BCS classes II and IV compounds or other agents that similarly exhibit poor solubility. The BCS definition describes a compound in which the effective dosing is not soluble in 250 mL of water at a pH from 1-7.5. The USP categories "very slightly soluble" and "insoluble" describe a material that requires 1,000 or more parts of the aqueous liquid to dissolve 1 part solute. As used herein, when a compound is described as poorly soluble, it refers to a compound which has solubility in water of less than 1 mg/mL. In other embodiments, the therapeutically active agent is an active agent which has a high melting point. Some non-limiting examples of high melting point therapeutically active agents are griseofulvin and theophylline.

When a therapeutically active agent is present in the composition, the therapeutically active agent is present in the composition at a level between 0.5% to 55% w/w, between 5% to 50% w/w, between 10% to 40% w/w, or between 15% to 35% w/w. In some embodiments, the amount of the pharmaceutically acceptable thermoplastic polymer is from about 0.5%, 1%, 5%, 10%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, to about 55% w/w or any range derivable therein.

The methods of the present disclosure may be used to manufacture many classes of therapeutically active agents including, but not limited to chemotherapeutics, anti-microbials such as antibacterials, antifungals, and anti-parasitics, anti-inflammatory agents such as non-steroidal anti-inflammatory agents, anti-hypertensives, anti-thrombotics, anticoagulants, anti-convulsants, neuromuscular therapeutics, anti-pyretics, anti-nauseants, vasodilators, anti-arrythmics, vasoconstrictors, anti-anginal therapeutics, gastrointestinal sedatives, anti-spasmodics, analgesics, diuretics, hypnotics, hyper- and hypoglycemic therapeutics, and thyroid and anti-thyroid agents. Some non-limiting examples of therapeutically active agents include albendazole, p-aminosalicylic acid, naproxen, carbamazepine, paclitaxel and other taxanes, carvedilol, ticagrelor, phenytoin, nimesulide, domperidone, candesartan teimisartan, amiodarone, felodipine, diazepam, metaxalone, aceclofenac, hydrochlorothiazide, zaleplon, glipizide, repaglinide, glibenclamide, and praziquantel.

In some aspects, the method may be most advantageously used with materials which undergo degradation at an elevated temperature or pressure. The therapeutically active agents that may be used include those which decompose at a temperature above about 50° C. In some embodiments, the therapeutically active agent decomposes above a temperature of 80° C. In some embodiments, the therapeutically active agent decomposes above a temperature of 100° C. In some embodiments, the therapeutically active agent decomposes above a temperature of 150° C. The therapeutic active agent that may be used include those which decompose at a temperature of greater than about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C.

B. Pharmaceutically Acceptable Thermoplastic Polymers

In some aspects, the present disclosure provides compositions which may further comprise a pharmaceutically acceptable thermoplastic polymer. In some embodiments, the polymer has been approved for use in a pharmaceutical formulation and is known to undergo softening or increased pliability when raised above a specific temperature without substantially degrading.

When a pharmaceutically acceptable thermoplastic polymer is present in the composition, the pharmaceutically acceptable thermoplastic polymer is present in the composition at a level between 1% to 60% w/w, between 5% to 55% w/w, between 10% to 50% w/w, between 20% to 40% w/w, between 25% to 35% w/w. In some embodiments, the amount of the pharmaceutically acceptable thermoplastic polymer is from about 1%, 5%, 10%, 15%, 20%, 21%, 22%, 23%, 24%, 25%, 26%, 27%, 28%, 29%, 30%, 31%, 32%, 33%, 34%, 35%, 36%, 37%, 38%, 39%, 40%, 45%, 50%, 55%, to about 60% w/w or any range derivable therein.

Within the compositions described herein, a single polymer or a combination of multiple polymers may be used. In some embodiments, the polymers used herein may fall within two classes: cellulosic and non-cellulosic. These classes may be further defined by their respective charge into neutral and ionizable. Ionizable polymers have been functionalized with one or more groups which are charged at a physiologically relevant pH. Some non-limiting examples of neutral non-cellulosic polymers include polyvinyl pyrrolidone, polyvinyl alcohol, copovidone, and poloxamer. Within this class, in some embodiments, pyrrolidone containing polymers are particularly useful. Some non-limiting examples of ionizable cellulosic polymers include cellulose acetate phthalate and hydroxypropyl methyl cellulose acetate succinate. Finally, some non-limiting examples of neutral cellulosic polymers include hydroxypropyl cellulose, hydroxypropyl methyl cellulose, hydroxyethyl cellulose, and hydroxymethyl cellulose.

In some embodiments, the compositions described herein contain a pharmaceutically acceptable thermoplastic polymer selected from povidone, copovidone, hydroxypropylmethyl cellulose, hypromellose acetate succinate, and SOLUPLUS (commercially available from BASF).

C. Solvent

The solvent used in the present methods and compositions allows the formation of mixtures comprising drug, polymer if present, and solvent under lower thermal and mechanical stresses than typically used in conventional melt extrusion process. Such mixtures also may be molecular level dispersions of the drug and polymer. In general, the solvent should be miscible with both drug and polymers. The degree of miscibility of the drug and polymer may be similar or different. In some embodiments, it is contemplated that when composition comprises a drug and a polymer that the organic solvent have a similar solubility for both components. Furthermore, the extent of miscibility of the solvents with both drug and polymer may be adjusted and optimized through methods known to a person of skill in the art. Miscibility between drug, polymer, and solvent allows for the formation of a homogeneous system consisting of drug, polymer, and solvent during the extrusion process. The homogeneity can defined using the qualities of extrudate, such as the uniformity of the contents and physical attributes.

In some embodiments, the organic solvent is a volatile solvent. In some embodiments, the organic solvent has a boiling point of less than 100° C. The boiling point of the solvent may be less than 100° C., 98° C., 96° C., 94° C., 92° C., 90° C., 88° C., 86° C., 84° C., 82° C., or 80° C. Some non-limiting examples of organic solvents include alcohols, ethers, haloalkanes, or carbonyl containing compounds each with 6 or fewer carbon atoms. In some embodiment, the solvents are organic solvents including, but not limited to methanol, acetonitrile, 2-butanol, 5-butyl alcohol, 1,2-dichloroethane, 1,4-dioxane, isopropanol, methanol, 1-propanol, 2-propanol, ethanol, acetone, isopropyl alcohol, dichloromethane, and combinations thereof. In some embodiments, the solvent may comprise a mixture of more than one solvent. In some embodiments, water may also be added to the solvent mixture to improve the solubility of either the therapeutically active agent or the pharmaceutically acceptable thermoplastic polymer in the solvent mixture.

In one aspect, the present methods and compositions are prepared using a mixture which contains a therapeutically active agent and an organic solvent wherein the mixture has a glass transition temperature ($T_g$) of less than 120° C. In some embodiments, the $T_g$ is from about 40° C. to about 120° C. In some embodiments, the $T_g$ is from about 40° C., 42° C., 44° C., 46° C., 48° C., 50° C., 52° C., 54° C., 56° C., 58° C., 60° C., 62° C., 64° C., 66° C., 68° C., 70° C., 72° C., 74° C., 76° C., 78° C., 80° C., 82° C., 84° C., 86° C., 88° C., 90° C., 92° C., 94° C., 96° C., 98° C., 100° C., 102° C., 104° C., 106° C., 108° C., 110° C., 112° C., 114° C., 116° C., 118° C., to about 120° C., or any range derivable therein. In some embodiments, the $T_g$ is about 80° C. The glass transition temperature of the composition, such as mixtures of drug, polymer, and the organic solvent, may be measured using differential scanning calorimetry. While the solvent added to the composition may affect the glass transition temperature, without wishing to be bound by any theory, it is believed that the solvent also acts to solubilize the different components of the reaction mixture and promote a homogenous composition rather than acting as a plasticizing agent. The solvent may be added in an amount sufficient to obtain an appropriate glass transition temperature for extrusion.

In some aspects, the amount of solvent needed to obtain an appropriate glass transition temperature is from about 0.5% to about 45% w/w. The mixture that may be used comprises from about 0.5%, 1%, 2%, 3%, 4%, 5%, 6%, 7%, 8%, 9%, 10%, 11%, 12%, 13%, 14%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 31%, 32%, 33%, 34%, 35%, 36%, 37%, 38%, 39%, 40%, 41%, 42%, 43%, 44%, to about 45% w/w, or any range derivable therein. In one embodiment, the solvent used for the processing is at 5 to 30% w/w of the initial mixture subjected to the extrusion process.

In addition to the solvent, other functional excipients such as lubricant, disintegrants, supercritical liquids, and surfactants may be included in the composition and process to facilitate processing and/or contribute to the in vivo performance of final dosage forms. In some embodiments, a filler, a binder, or excipients may also be added to the composition.

II. EXTRUSION METHODS

Thus, in one aspect, the present disclosure provides a method of manufacturing an extrudate or amorphous solid dispersion. The method generally comprises the steps of combining a therapeutically active agent and an organic solvent (e.g., single or co-solvent system) in a mixing apparatus thereby forming a mixture. This mixture may further comprise a pharmaceutically acceptable thermoplastic polymer if appropriate. The mixture is then extruded to form an extrudate comprising the therapeutically active agent. Additionally, as described herein, this extrudate may be further manufactured into a pharmaceutical composition for administration to a patient. The pharmaceutical composition comprises a therapeutically active agent; a polymer; and an organic solvent, wherein the organic solvent is present upon formation of the amorphous solid dispersion and can be reduced to regulatory acceptable levels by further processing steps.

The solvent can be added to the therapeutically active agent and polymer in a number of different manners. In one non-limiting example, the therapeutically active agent and polymer can be initially granulated by addition of the organic solvent prior to the extrusion process. In an alternative non-limiting example, a bulk powder comprising therapeutically active agent and polymer can be added to the mixer/extruder through a side stuffer or some other bulk inlet port and the organic solvent can then be added through a solvent injection port as the extrusion process begins. Still yet another non-limiting example is to add the solvent online to the extruder downstream of the bulk powder comprising the polymer and active agent. Without wishing to be bound by any theory, it is believed that the introduction of the solvent into the composition results in reduced torque and/or reduced visocosity. In some embodiments, the amount of torque is equal to or less than 85% of the torque rating for the extruder motor.

In some embodiments, the solvent may be used to impart porosity to the final formulation. For example, the internal porosity may be affected by evaporation of a volatile solvent, which in turn may be used to affect the compression properties of a final formulation.

The mixing and thermal processing can be formed with an acceptable mixing/extruding apparatus including but not limited to a single screw extruder, an intermeshing screw extruder, a twin-screw extruder, a thermokinetic mixer, and a kneader. One specific example of a suitable mixer/extruder apparatus is the Plasti-Corder® Lab-Station with twin-screw extruder (Brabender®GMBH & Co.; Duisburg, Germany).

In some aspects, the extruder may comprise heating the composition to a temperature from about 60° C. to about 180° C. In some embodiments, the temperature is from about 80° C. to about 120° C. The temperature that may be used is from about 60° C., 65° C., 70° C., 75° C., 80° C., 82° C., 84° C., 86° C., 88° C., 90° C., 92° C., 94° C., 96° C., 98° C., 100° C., 102° C., 104° C., 106° C., 108° C., 110° C., 112° C., 114° C., 116° C., 118° C., 120° C., 125° C., 130° C., 135° C., 140° C., 145° C., 150° C., 155° C., 160° C., 165° C., 170° C., 175° C., to about 180° C. or any range derivable therein.

The extrudate produced following the extrusion process will generally comprise the therapeutically active agent and the pharmaceutically acceptable thermoplastic polymer if used. This extrudate may be used in further processing steps to yield the final pharmaceutical product or composition. The extrudate may be further dried to remove the solvent during the preparation of the final pharmaceutical product or composition. Such drying may be carried out in at an elevated temperature, a reduced pressure, or both.

Following the thermal processing, a portion of the solvent is evaporated off as the extrudate exist the extruder die. Some of the solvent, approximately 10 to 90% of the solvent initially present in the extrusion stock material composition, remains in the extrudate and then is removed using a subsequent drying process. Thus, the extrudate or other post-thermal processing intermediate product will include solvent from about 0.5% to about 27%. The solvent may or may not be homogeneously dispersed at molecular level in the extrudate.

Following any necessary drying steps, the resulting extrudate is milled or ground to granules or a dry powder. The granules or dry powder may then be compacted. Compacting refers to a process whereby a powder mass comprising the granules or powder is densified under high pressure in order to obtain a compact with low porosity, e.g. a tablet. In some embodiments, the product is formulated in a manner which is amenable to oral administration. Compression of the powder mass is usually done in a tablet press, more specifically in a steel die between two moving punches.

III. EXAMPLES

To facilitate a better understanding of the present invention, the following examples of specific embodiments are given. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. In no way should the following examples be read to limit or define the entire scope of the invention.

Example 1—Degradation of Thermally Unstable Drug

A. Materials.

Albendazole (Molekular, Irvine, Calif.) was selected as a model drug. Kollidon VA 64 was donated by BASF (Florham Park, N.J.). Triethyl citrate (TEC) was purchased from Vertellus (Greensboro, N.C.), and Ethanol, absolute was purchased from Acros organics (Fair Lawn, N.J.). Other chemicals and solvents used were ACS reagent or HPLC grade.

B. Preparation of Blends.

Albendazole and Kollidon VA 64 were dried in the oven (ON-12G, Jero tech, Kyunggi-do, Korea) at 70° C. for 20 hours before use. The blends were mixed in a plastic ziplock bag using a geometric dilution technique. The albendazole content in the blend was 20% (w/w).

C. Production of Extrudates.

Extrudates of the albendazole blends were made using Leistriz Nano 16 twin-screw extruder (Nuremberg, Germany) configured as shown in FIG. 1. The extruder was set up with four zones. The first zone is the "feeding zone" and was cooled with a water jacket to maintain the temperature below 35° C. The remaining three zones were maintained at various elevated temperatures depending on the particular extrusion being performed. The configuration of screws used in the present example is shown in FIG. 1.

Table 1 shows an overview of all parameters varied during an extrusion study of the albendazole blend. Runs 1-3 are controls. In Runs 4-8 ethanol was introduced during the extrusion through an injection nozzle in zone 2. In Runs 9-12 TEC (plasticizer) was introduced an injection nozzle in zone 2. Both the solvent and the plasticizer were delivered using a Shimadzu (Kyoto, Japan) HPLC pump.

TABLE 1

Extrusion temperature, screw speed, solvent/liquid used, flow rate of solvent/liquid, torque and pressure during extrusion

| Extrusion Run | Extrusion Zone Temperature (° C.) | | | | | Screw speed (RPM) | Solvent or Liquid | Flow rate (ml/min) | Torque (Nm) | Melt pressure (psi) | Feed rate (g/min) |
|---|---|---|---|---|---|---|---|---|---|---|---|
| | Die | 4 | 3 | 2 | 1 | | | | | | |
| 1 | 120 | X | 120 | 120 | 110 | 100 | — | — | 1450 | 300 | 1.5 |
| 2 | 120 | X | 120 | 120 | 110 | 200 | — | — | 1350 | 200 | 1.5 |
| 3 | 120 | X | 120 | 120 | 110 | 300 | — | — | 1150 | 200 | 1.5 |
| 4 | 120 | X | 120 | 120 | 110 | 150 | Ethanol | 0.2 | 750 | 50 | 1.5 |
| 5 | 120 | X | 120 | 120 | 110 | 150 | Ethanol | 0.5 | 650 | 65 | 1.5 |
| 6 | 120 | X | 120 | 120 | 110 | 300 | Ethanol | 0.5 | 550 | 45 | 1.5 |
| 7 | 110 | X | 110 | 110 | 100 | 300 | Ethanol | 0.5 | 600 | 40 | 1.5 |
| 8 | 100 | X | 100 | 100 | 100 | 300 | Ethanol | 0.5 | 670 | 30 | 1.5 |
| 9 | 100 | X | 100 | 100 | 100 | 300 | TEC | 0.2 | 700 | 50 | 1.5 |
| 10 | 100 | X | 100 | 100 | 100 | 150 | TEC | 0.2 | 1000 | 40 | 1.5 |
| 11 | 110 | X | 110 | 110 | 100 | 150 | TEC | 0.2 | 900 | 30 | 1.5 |
| 12 | 110 | X | 110 | 110 | 100 | 300 | TEC | 0.2 | 650 | 34 | 1.5 |

D. Chemical Stability.

Samples of the albendazole blends following hot melt extrusion were analyzed by HPLC. The method was modified from the USP 36 monograph of albendazole tablets ("USP-NF," n.d.). The HPLC system (Ultimate 3000, Dionex Corp., Sunnyvale, Calif.) was equipped with a UV-Vis detector, an Inertsil® ODS-2 (4.6×150 mm) column (GL Sciences, Tokyo, Japan). The mobile phase was 4.35 mM monobasic ammonium phosphate and methanol (40: 60% v/v). To prepare the sample solutions, the extrudates were finely milled in the mortar and pestle. An accurate weight of the powder, equivalent to about 20 mg of albendazole, was transferred to a 10-mL volumetric flask. One mL of sulfuric acid in methanol (1% v/v) was added to dissolve the drug and dilute with methanol to volume. The clear solution was transferred to a second 10-mL volumetric flask, diluted with methanol to volume. The concentration range of standard curves was between 1.5 and 400 µg/mL. The percentage of albendazole remaining in the sample was calculated. (Table 2)

E. X-Ray Diffraction.

The crystalline properties of the bulk albendazole, Kollidon VA 64, the blend of albendazole and Kollodon VA 64, and the extrudates were examined by X-ray diffraction (XRD). A Rigaku R-AXIS Spider X-ray diffractometer with a copper X-ray source (Rigaku Americas, Woodlands, Tex.) was used to receive the XRD patterns. The voltage and current were set to 40 kV and 40 mA, respectively. Samples were determined in the 2θ range from 10 to 40°.

F. Results

Figure 2:
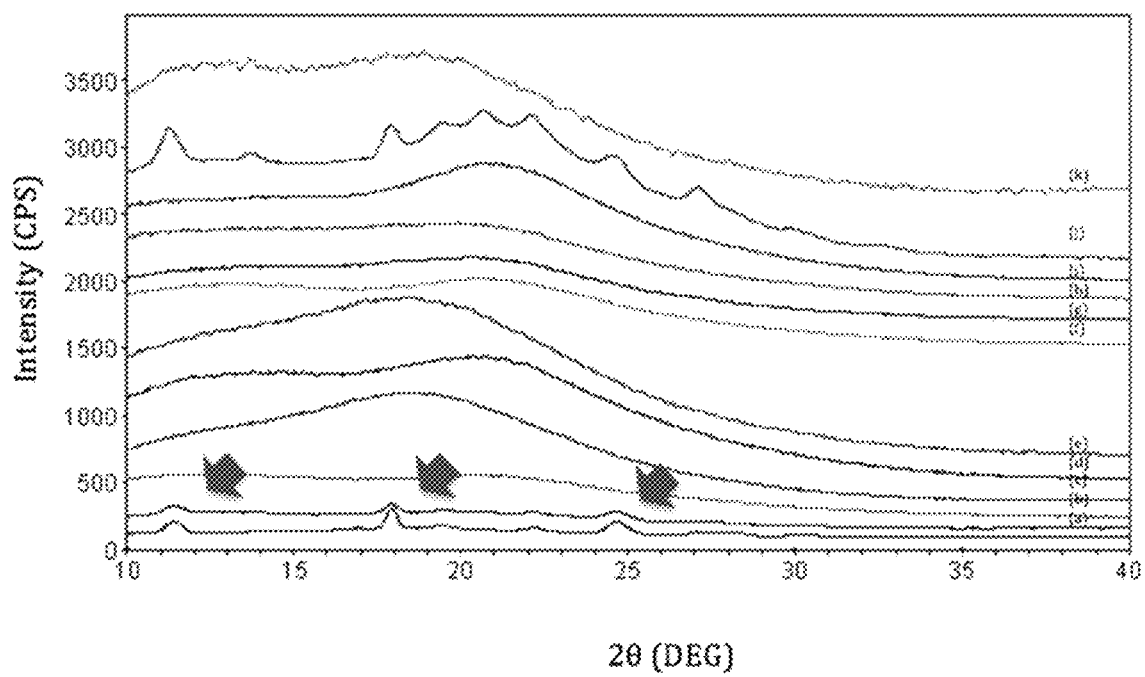
FIG. 2 shows X-ray diffraction patterns of (a) bulk crystalline albendazole (b) albendazole: Kollidon VA 64 (20:80) (c) extrudate formulation 1 (d) extrudate formulation 2 (e) extrudate formulation 3 (f) extrudate formulation 4 (g) extrudate formulation 5 (h) extrudate formulation 6 (i) extrudate formulation 7 (j) extrudate formulation 8 (k) Kollidon VA 64. The arrows indicate crystalline albendazole major peaks.
Figure 3:
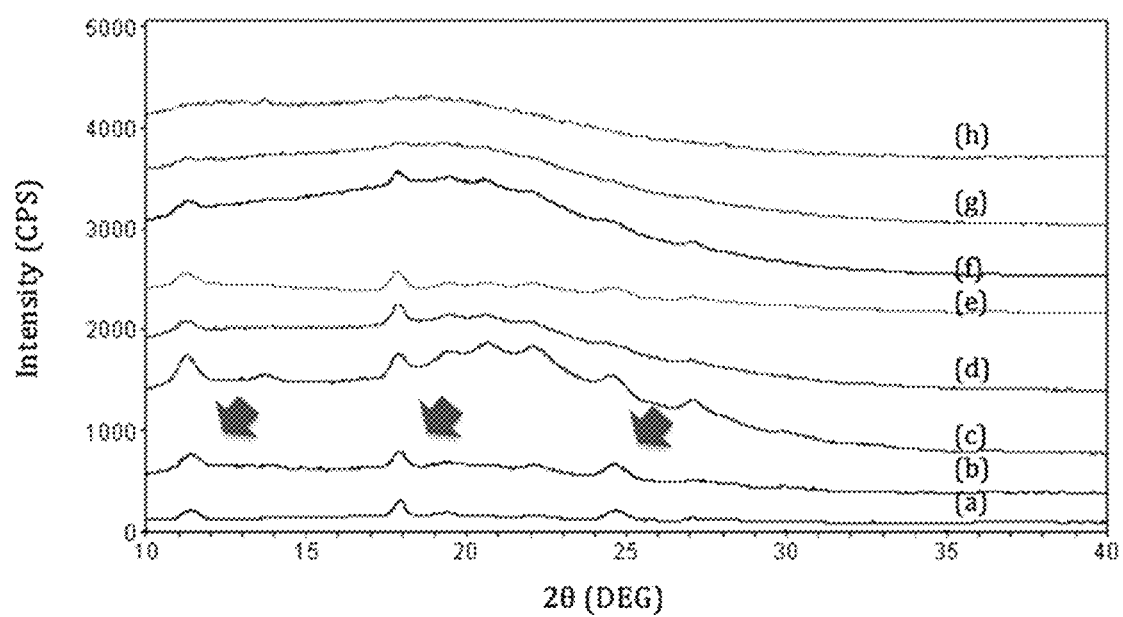
FIG. 3 shows X-ray diffraction patterns of (a) bulk crystalline albendazole (b) albendazole: Kollidon VA 64 (20:80) (c) extrudate formulation 9 (d) extrudate formulation 10 (e) extrudate formulation 11 (f) extrudate formulation 12 (g) extrudate formulation 13 (h) Kollidon VA 64. The arrows indicate crystalline albendazole major peaks.

Albendazole is known to hydrolyze when exposed to elevated temperatures. This was seen in control runs 1-3 where albendazole was degraded. In contrast, the presence of ethanol in runs 4-8 resulted in reduced albendazole degradation. Reduced albendazole degradation was also achieved when using TEC as a plasticizer as seen in runs 9-12. However, TEC was not able to maintain albendazole in an amorphous state. For crystallinity results, see FIGS. 2 and 3.

TABLE 2

Percent albendazole remaining, crystallinity, and physical appearance

| Extrudate Run | % ABZ remaining | Solvent or Liquid | XRD | Physical Appearance |
|---|---|---|---|---|
| Blend | 100.00 | | | |
| 1 | 9.49 | — | Amorphous | Clear extrudate |
| 2 | 4.45 | — | Amorphous | Clear extrudate |
| 3 | 2.63 | — | Amorphous | Clear extrudate |
| 4 | 26.54 | Ethanol | Amorphous | Clear extrudate |
| 5 | 35.46 | Ethanol | Amorphous | Clear extrudate |
| 6 | 28.17 | Ethanol | Amorphous | Clear extrudate |
| 7 | 28.95 | Ethanol | Amorphous | Translucent extrudate |
| 8 | 56.62 | Ethanol | Crystalline | Opaque extrudate |
| 9 | 57.73 | TEC | Crystalline (very small peaks) | Opaque extrudate |
| 10 | 75.66 | TEC | Crystalline | Opaque extrudate |
| 11 | 50.09 | TEC | Crystalline (very small peaks) | Opaque extrudate |
| 12 | 34.99 | TEC | Crystalline (very small peaks) | Translucent extrudate |

Example 2—Processing Conditions

Hydroxypropyl methylcellulose acetate succinate (HPMC-AS) was extruded on a Nano16 co-rotating twin screw extruder (Leistritz Advanced Technologies Corp.) at multiple conditions with and without solvent injection. The screw speed and feed rate were maintained at 150 RPM and 3 g/min respectively. The conditions are shown in Table 3.

TABLE 3

| Extrusion Processing Conditions | |
| --- | --- |
| Screw Speed | 150 RPM |
| Feed Rate | 3 g/min |
| Barrel Temperature (Z1, Z2, Z3, die) | 150° C., 140° C. |
| Solvent Inj. Rate | 0.8 mL/min |

Figures 4A, 4B:
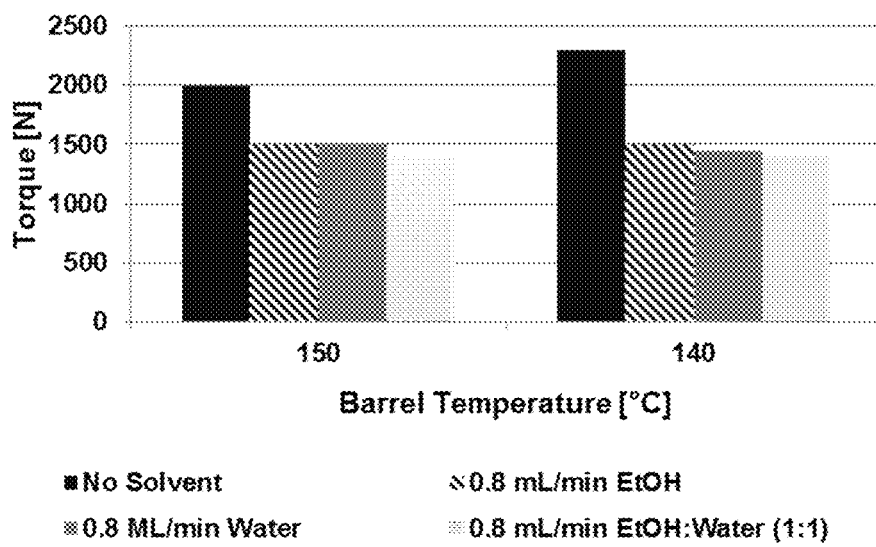
FIGS. 4A and 4B show the screw configuration and torque exerted under specific process conditions.

The screw design was also kept constant (FIG. 4A). The screw design was configured to maintain a seal in the solvent injection zone. Two different barrel temperatures were used (150° C. and 140° C.). The torque was recorded at each condition when the system reached steady state (no less than 10 minutes after reaching target condition). At each temperature HPMC-AS was extruded without solvent and again with 0.8 mL/min ethanol, water, and an ethanol/water mixture (1:1, ethanol:water by volume). In all cases torque and therefore processing conditions were reduced with solvent injection (FIG. 4B). At 150° C. torque was reduced approximately 500 N and at 140° C. torque was reduced over 1000 N with injection of ethanol or water.

Example 3—Extrusion of Amorphous Solid Dispersion

A blend of naproxen and povidone (PVP K25) was prepared (30:70, naproxen:povidone by weight). The blend was extruded on a Nano16 co-rotating twin screw extruder (Leistritz Advanced Technologies Corp.) with solvent injection to prepare an amorphous solid dispersion (ASD). Screw speed and feed rate were maintained at 150 RPM and 3 g/min respectively. The conditions are shown in Table 4.

TABLE 4

| Amorphous Solid Dispersion Processing Conditions | |
| --- | --- |
| Screw Speed | 150 RPM |
| Feed Rate | 3 g/min |
| Barrel Temperature (Z1, Z2, Z3, die) | 110° C. |
| Solvent Inj. Rate | 0.8 mL/min |

Figures 5A, 5B:
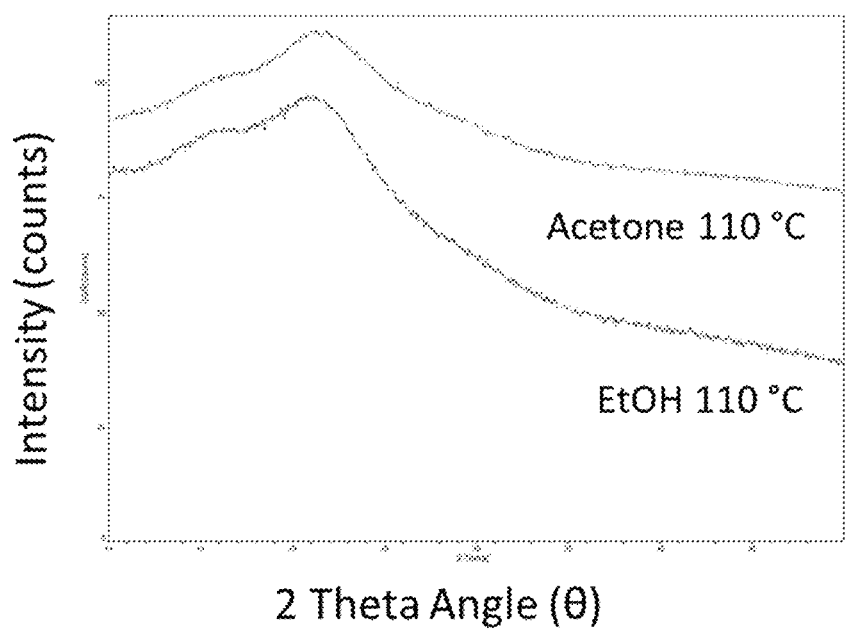
FIGS. 5A and 5B show the screw configuration and the X-ray powder diffraction of naproxen and pharmaceutically acceptable thermoplastic polymer polyvinyl pyrollidone.

The screw design was also kept constant (FIG. 5A). The screw design was configured to maintain a seal in the solvent injection zone. The barrel temperature was also kept constant at 110° C. Acetone or ethanol was injected into zone 2 at 0.8 mL/min. The resultant extrudate was milled and powder X-ray diffraction (PXRD) was performed to confirm amorphous material (FIG. 5B). Materials extruded with both solvents resulted in an ASD.

Prophetic Example 4—Drug Dissolved in Solvent

In another embodiment, a thermally labile or difficult to extrude drug will be dissolved in solvent (1-30% w/v). Polymer will be fed to a co-rotating twin screw extruder (the extruder to be used should include a solids-conveying mechanism that extends from the hopper through the heating zones to the extrusion die). After melting, the drug-solvent solution will be injected into the extruder through an injection port (after zone 1). Solvent injection rate will be controlled with a high performance liquid chromatography (HPLC) pump and will be adjusted based on drug and polymer miscibility as well as the desired final drug loading. The solvent or co-solvent system will be selected based on drug and polymer solubility. The barrel temperature will be set above the glass transition of the polymer. Screw design will be chosen to ensure a seal in the injection zone. Screw speed will be dependent on formulation and can range from 50-350 RPM. The resulting extrudate will be milled and checked for degradation by HPLC.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of preparing an extrudate comprising:
   (a) obtaining an extrusion stock material composition comprising:
      (1) a mixture of a therapeutically active agent, wherein the therapeutically active agent is a compound that undergoes decomposition above 50° C.; and a pharmaceutically acceptable thermoplastic polymer, wherein the pharmaceutically acceptable thermoplastic polymer is polyvinyl pyrrolidone or copovidone, comprising from about 0.5% to about 55% w/w of a therapeutically active agent; and
      (2) an organic solvent;
   wherein the composition has a glass transition temperature ($T_g$) from about 40° C. to about 100° C.; and
   (b) transferring the extrusion stock material composition through an extruder to obtain an extrudate comprising the therapeutically active agent and the organic solvent; and
   (c) heating the extrusion stock material composition as the extrusion stock material composition is transferred through the extruder to a temperature from about 50° C. to about 180° C.

2. The method of claim 1, wherein the extruder is a single screw extruder, an intermeshing screw extruder, a twin-screw extruder, a thermokinetic mixer, and a kneader.

3. The method of claim 1, wherein the temperature is from about 80° C. to about 160° C.

4. The method of claim 1, wherein the method further comprises cooling the extrudate to room temperature.

5. The method of claim 1, wherein the method further comprises drying the extrudate to remove the organic solvent.

6. The method of claim 5, wherein drying the extrudate is done at an elevated temperature.

7. The method of claim 6, wherein the elevated temperature is from about 30° C. to about 100° C.

8. The method of claim 5, wherein drying the extrudate is done at a reduced pressure.

9. The method of claim 8, wherein the reduced pressure is from about 1 kPa to about 100 kPa.

10. The method of claim 5, wherein drying the extrudate is done at an elevated temperature and at a reduced pressure.

11. The method of claim 1, wherein the method further comprises milling the extrudate to obtain a dry powder or a granule.

12. The method of claim 11, wherein the method further comprises formulating the dry powder or granule into a pharmaceutical composition.

13. The method of claim 1, wherein the method comprises applying a torque of less than 85% of the capacity of the motor of the extruder.

14. The method of claim 1, wherein the pharmaceutically acceptable thermoplastic polymer and the therapeutically active agent are added first and then the organic solvent.

15. The method of claim 1, wherein the pharmaceutically acceptable thermoplastic polymer and the therapeutically active agent are added after the organic solvent.

16. The method of claim 1, wherein the organic solvent is a volatile organic solvent.

17. The method of claim 16, wherein the organic solvent is a mixture of solvents comprising at least one solvent selected from the group consisting of methanol, ethanol, isopropanol, acetone, tetrahydrofuran, or dichloromethane or is a mixture with water.

18. The method of claim 1, wherein the therapeutically active agent is antifungal agent or a non-steroidal anti-inflammatory.

* * * * *